United States Patent [19]
Eddelman

[11] 3,985,649
[45] Oct. 12, 1976

[54] FERROMAGNETIC SEPARATION PROCESS AND MATERIAL

[76] Inventor: Roy T. Eddelman, 60916 Terminal Annex, Los Angeles, Calif. 90054

[22] Filed: Nov. 25, 1974

[21] Appl. No.: 526,787

[52] U.S. Cl. .......................... 210/42 S; 259/DIG. 46
[51] Int. Cl.² ........................................ B01D 35/06
[58] Field of Search ............. 259/1 R, DIG. 46, 72; 23/252 R; 428/329; 310/98, 104, 103, 105; 210/222, 23, 24, 223, 42; 206/818; 424/8

[56] References Cited
UNITED STATES PATENTS

| | | | |
|---|---|---|---|
| 3,219,318 | 11/1965 | Hershler | 259/1 R |
| 3,428,179 | 2/1969 | Boyd | 210/222 |
| 3,487,939 | 1/1970 | Keeley | 210/222 |
| 3,712,472 | 1/1973 | Elliott | 210/222 |
| 3,793,886 | 2/1974 | Rosenwald | 259/DIG. 46 |
| 3,869,251 | 3/1975 | Tsantker | 23/252 R |
| 3,892,908 | 7/1975 | Lovness | 428/329 |

*Primary Examiner*—Robert W. Jenkins

[57] ABSTRACT

A method of carrying out a solid phase chemical reaction or a filtration step to remove a solid from a liquid utilizing ferromagnetic particles. The particles may have a porous or otherwise bondable solid support material having adsorbed or chemically bonded thereon a biologically active substance to make them biologically active. Alternatively, the particles may act as an inert medium to convey a solid precipitate out of a liquid. The process involves the addition of the ferromagnetic particles to a potentially reactive fluid. After the fluid has reacted either as a result of contact with the biologically active material or by a process causing a precipitate in the fluid, the particles may be separated from the fluid by bringing the particles into close proximity with a magnet such as an electromagnet. When sufficient particles are held in an elongated container and a magnetic force is exerted to hold the particles in a porous mass across the container, the particles may be moved through the liquid to filter solid particles from the liquid. A second container may be placed over a portion of the elongated container on the particles and any entrapped precipitate may be removed from the elongated container. The particles may alternatively have a bondable surface capable of adsorption or chemical coupling of biologically active materials. Polymer and ceramic biomaterial supports and particular combinations with ferromagnetic materials are disclosed. A valve formed from the ferromagnetic particles is also disclosed herein.

11 Claims, 13 Drawing Figures

U.S. Patent  Oct 12, 1976  Sheet 1 of 2  3,985,649
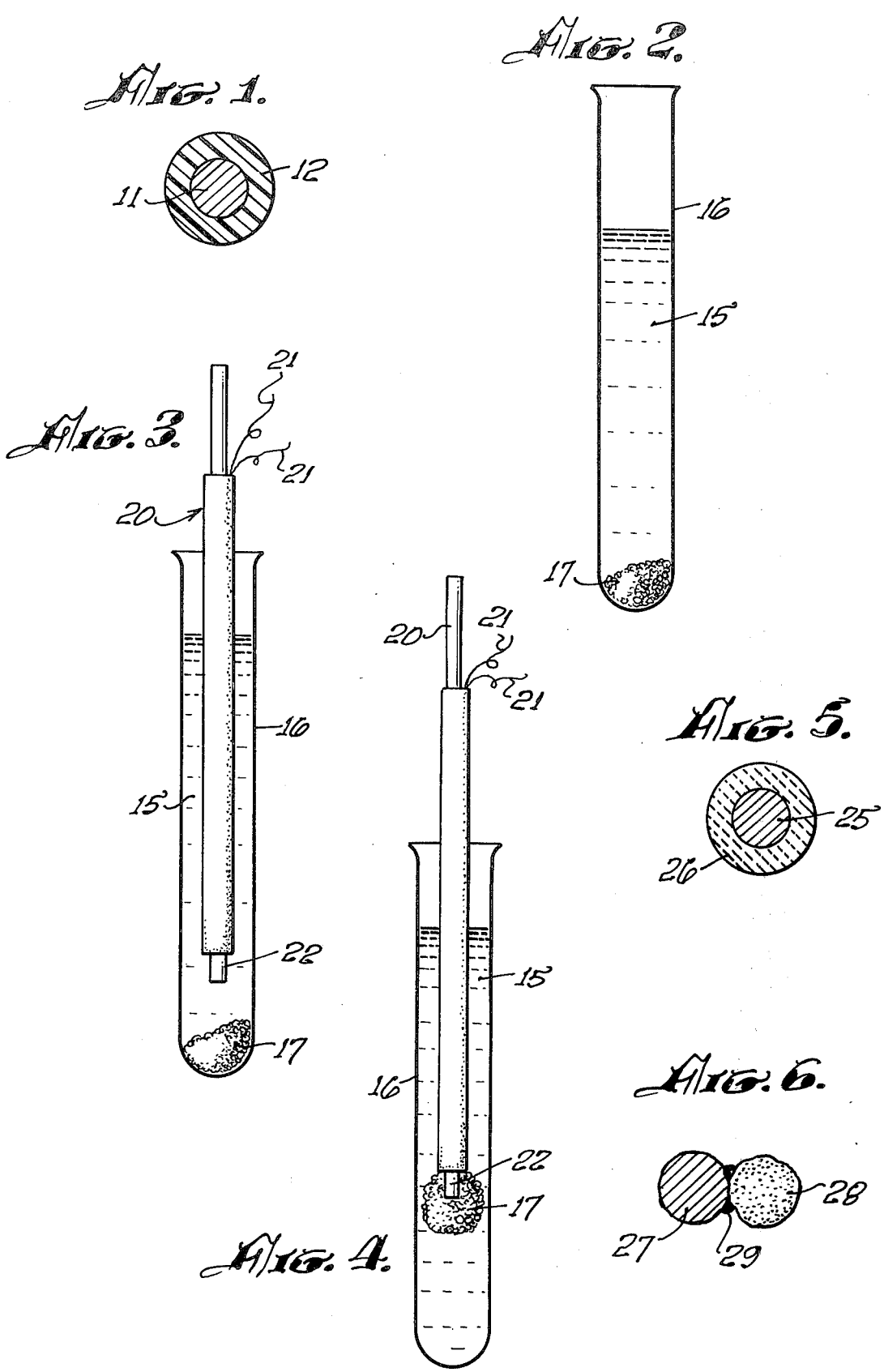

U.S. Patent  Oct 12, 1976  Sheet 2 of 2  3,985,649
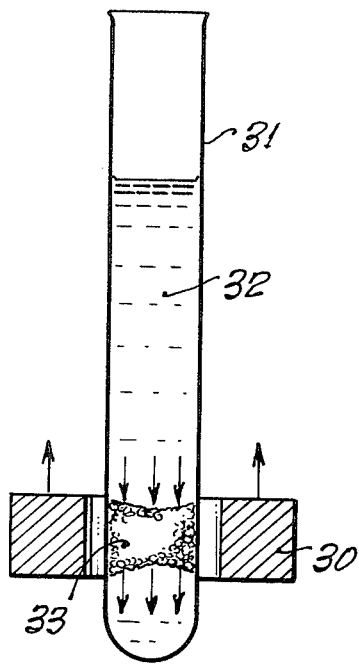
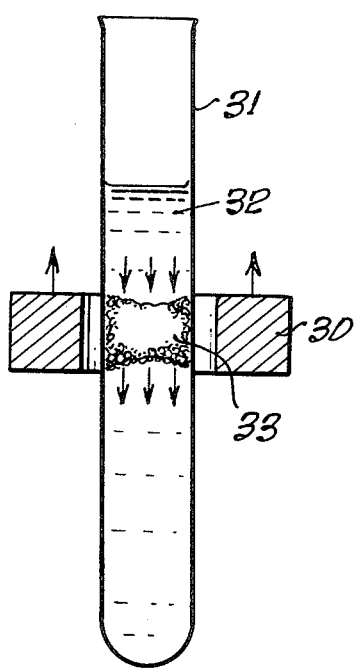
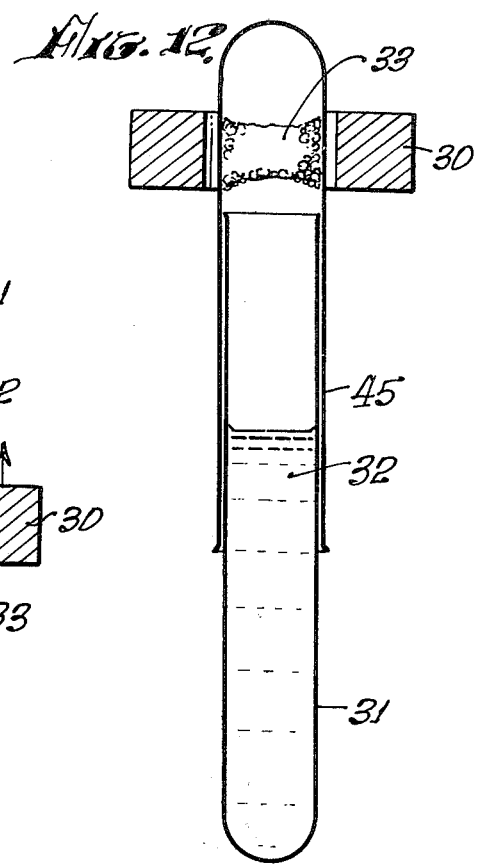
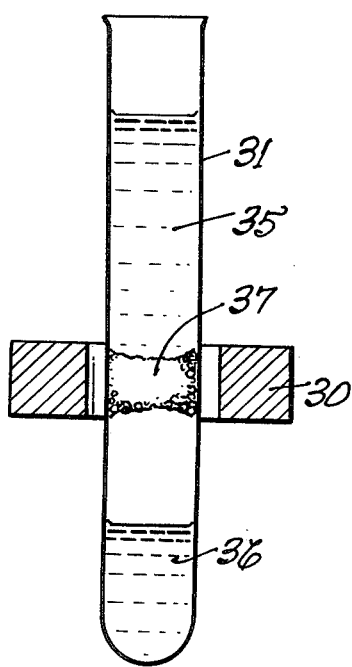
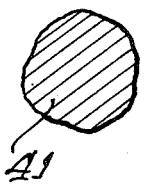
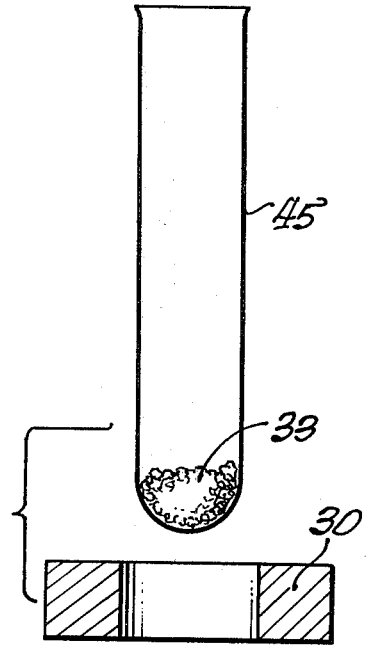

FERROMAGNETIC SEPARATION PROCESS AND MATERIAL

BACKGROUND OF THE INVENTION

The field of the invention is chemical processing of the type where a fluid is mixed with one or more solid particles. One such process utilizes biomaterial supports through the interaction of a biologically active chemical held to the surface of the biomaterial support. Another such process is the basic removal of a solid from a liquid. Biomaterial supports may be inorganic or organic and have been made from glass, having a plurality of pores or other chemically active sites on the surface thereof, and such supports have also been made from polymers which have the capability of holding a desired biologically active molecule along the surface of the support material. The term "biomaterial support" as used herein refers to any substance which has the ability to hold substances which enter into or effect a chemical reaction. This ability may be brought about by micro pores on the surface of the material or by a chemical attraction, reaction, or adsorption of molecules on the surface material.

Various biomaterial supports have been found to have the ability to selectively hold and, in some cases, orient chemicals such as enzymes, antibodies, and binding proteins. These adsorbed substances then can become available to bring about a desired chemical reaction. Biomaterial supports having adsorbed substances are particularly useful for carrying out radioimmunoassay techniques. For example, an adsorbed or bonded antibody material is brought into contact with a liquid containing a known quantity of antigen. The radioactive antigen will compete with the unknown quantity of unlabeled antigen to bind to the antibody coupled to the support. After the competitive binding phase, the biomaterial support is removed from the liquid. This removal has, in the past, utilized techniques such as filtration, centrifugation or decantation.

The use of biomaterial supports is applicable to many processes for separating or reacting large numbers of samples and there is thus a desire to automate many such processes in order to carry them out more efficiently. Attempts to bring about automation of such processes have met with numerous obstacles many of which result from the step of separating the biomaterial support from the liquid reactant. Centrifugation requires several separate steps including placing the sample into a centrifuge followed by a decantation or other removal of the liquid from the solid biomaterial support. Also, centrifugation is not capable of distinguishing between a solid biomaterial support and other solid or more dense liquid components which may be present in the treat liquid.

Separation by filtration of numerous individual samples is generally cumbersome and is a difficult to automate procedure. Heretofor it has been necessary to move a liquid through a filter medium. Furthermore, numerous liquids such as fermentation broths contain substances which interfere with rapid and effective filtration. Like centrifugation, filtration is often incapable of separating a biomaterial support solid from other solids. Decantation is likewise a difficult to automate procedure and is thus usually done by hand. The effectiveness of separation by decantation is highly dependant upon operator's skill and this is inherently undesirable when a high degree of accuracy is required.

SUMMARY OF THE INVENTION

It is thus an object of the present invention to provide a method for separating a biomaterial support particle or particles from a fluid reactant.

It is another object of the present invention to provide a new biomaterial support particle.

It is a further object of the present invention to provide a filtration process to remove a solid from a liquid.

It is a still further object of the present invention to provide a magnetically operated valve.

The present invention is for a process and a material for carrying out a solid phase chemical reaction. The invention further comprises a ferromagnetic mixing or filtration process. The potentially reactive fluid is mixed with a biomaterial support particle which has adsorbed or bonded upon its surface a biologically active substance. The particle has a ferromagnetic substance affixed thereto causing the biomaterial support particle to be attracted by a magnet. Alternatively, the ferromagnetic substance itself could adsorb or bond a reactive component without the addition of a separate biomaterial support. The process involves adding the ferromagnetic biologically active material to the potentially reactive fluid and maintaining the particle in contact with the fluid for a time sufficient to carry out the desired reaction. The biomaterial support and its biologically active substance are removed from the liquid by placing a magnet in proximity to the particle or particles. By the use of automated equipment and an electromagnet, the process may be carried out with a great deal of efficiency on a large number of samples. A single particle or a plurality of particles may be used and the ferromagnetic particles may be partially or completely surrounded by the solid support material if such is required. The invention also calls for a biomaterial support particle comprising a ferromagnetic substance affixed to a solid support material which has a biologically active material affixed thereto. The biomaterial support may be a polymer such as poly methyl methacrylate, polystyrene, polypropylene, acrylamide polymer or an inorganic substance such as glass, ceramic or metal. When used as a mixing or filtration process, a plurality of ferromagnetic particles is placed in an elongated container and is moved through the container by a magnetic field. The filtration action may be improved by the addition of a filter aid.

BRIEF DESCRIPTION OF THE DRAWINGS

FIG. 1 is an enlarged cross-sectional view of a biomaterial support particle of the present invention.

FIG. 2 is a side elevation of a liquid reactant held in a test tube and containing a plurality of the biomaterial support particles of FIG. 1.

FIG. 3 is a side elevation of the tube of FIG. 2 further containing an electromagnet.

FIG. 4 is a side elevation of the tube and magnet of FIG. 3 with an electromagnet in an energized state.

FIG. 5 shows an alternate configuration of the particle of FIG. 1.

FIG. 6 is a cross-sectional view of an alternate configuration of the particle of the present invention.

FIG. 7 is a cross-sectional side elevation of a plurality of particles of the present invention held in a test tube surrounded by a magnet.

FIG. 8 is a cross-sectional view of the device of FIG. 6 with the magnet in an altered position.

FIG. 9 is a cross-sectional side elevation of a plurality of particles of the present invention held in a test tube and supporting a liquid.

FIG. 10 is a perspective view of an alternate configuration of the particle of the present invention.

FIG. 11 is a perspective view of an alternate configuration of the particle of the present invention.

FIG. 12 is a cross-sectional side elevation of the device of FIG. 8 further including an inverted test tube receptacle for the particles of the present invention.

FIG. 13 shows the test tube receptacle and particles of FIG. 12.

DESCRIPTION OF THE PREFERRED EMBODIMENTS

A ferromagnetic biomaterial support particle is shown in cross-sectional view in FIG. 1. An inner sphere of iron 11 is surrounded by a layer of a biomaterial support substance such as polymer 12. The iron core 11 can be fabricated from ferromagnetic materials other than iron such as cobalt or nickel or other alloys which have the property of ferromagnetism. It is generally desirable that the ferromagnetic material be made from a material having a low order of toxicity since many potential applications would require contact with substances which must be maintained in a non-toxic state.

The polymer layer 12 may be any substance which has the property of adsorbing or otherwise holding biologically active chemicals. It is possible that the ferromagnetic substance itself would have the property of binding the chemically active material directly without the necessity of a separate support layer. Such substances are referred to herein as "biomaterial supports". Examples of such materials include poly methyl methacrylate, polystyrene, polypropylene, acrylamide polymers, porous glass containing a large number of pores of an accurately controlled size, or glass or ceramic having active chemical sites for bonding the active substance. The surface of the porous glass may be treated to assist in binding or orienting and binding particular molecules. As biomaterial supports are currently the subject of intensive research, it is likely that other materials will be found which have this ability to adsorb or otherwise hold biologically active chemicals and thus the present invention is not dependent upon the particular biomaterial support used but instead upon the rendition of the biomaterial support to a ferromagnetic condition.

While the shape of the particles is not crucial for many applications, the majority of work today has been done with spheres. The size of the coated sphere is likewise not critical for most applications, but particle sizes between 0.1 and 10 millimeters in diameter is preferred with about 0.5 millimeter being best for many applications. When it is essential that each and every particle be removed from the liquid, it is preferable to use a larger size particle in order to create a larger magnetic force between the particle and the magnet. When used as a magnetically operated valve, the particles may be flat or plate-like such as that shown in FIG. 10.

The means by which the material is made magnetic may vary considerably. The majority of work to date has utilized iron spheres coated with a thermoplastic polymer but other means for bringing about ferromagnetic attraction may also be used. For instance, when a polymer is utilized as the support material, it could be blended with a very finely divided ferromagnetic substance so that the final polymer particle would be relatively uniform and yet still be attracted by a magnet.

Although it is preferable that the biomaterial support completely surround a ferromagnetic substrate for some applications it would be sufficient that the ferromagnetic and biomaterial support simply be attached and the ferromagnetic material could be exposed to the liquid. For such applications it is important that the ferromagnetic material be resistant to the fluid into which it is placed. While many applications can tolerate exposure to uncoated iron particles, a more corrosion resistant material such as nickel would be preferable for many applications. Alternatively, an iron particle could be protected with a corrosion resistant coating and, in turn, adhered to a biomaterial support and the resulting combination would be resistant to a large number of liquids. This latter method may be used also with ceramic support materials and one or more particles of the ceramic support could be adhered to the ferromagnetic material. Further, the iron or other ferromagnetic substance could itself hold or bind chemically active substances and thus not need a separate support material affixed thereto.

Various means may be used to coat a ferromagnetic material with a biomaterial support. One such means would involve heating a plurality of iron spheres and mixing them with a powdered thermoplastic resin such as poly methyl methacrylate. The iron spheres should be heated to a point which would cause the poly methyl methacrylate to melt and fuse to the outer surface of the iron particle. This mixture may be carried out in a fluidized bed by utilizing a finely divided resin which is aerated from below in a manner known to those skilled in the art. The heated iron particles could then be added to the fluidized bed and the finely divided resin particles would contact, melt and adhere to the outer surface of the iron particles.

Alternatively, the biomaterial support polymer could be dissolved or dispersed in a solvent and the ferromagnetic particles dipped therein, removed and dried. By utilizing ferromagnetic alloys of a high enough melting point, glass biomaterial support material could be fused to the outer surface of the ferromagnetic material in a manner similar to that described above for polymeric biomaterial supports.

Returning now to the drawings, a liquid 15 is held in a test tube 16 shown in FIG. 2. A plurality of particles of the type shown in FIG. 1 — that is ferromagnetic biomaterial support particles — are mixed with liquid 15. Prior to mixing, the particle is made biologically active by the adsorption or chemical coupling of molecules such as antigens, antibodies, enzymes or binding proteins. While not wishing to be bound by any theory, it is believed that these molecules are held to the biomaterial support by attachment to a group on the molecule which is not essential for biological activity. For instance a hydroxyl group, phenol ring, amine group or the like could be held by the support material and permit the active portion of the molecule to be available for reaction with molecules in the liquid into which the particle is placed.

After adsorption of the biologically active material, the particles 17 are mixed with liquid 15 and, depending upon the density of liquid 15, either settle to the bottom or rise to the top of the liquid. In the unlikely event that the gravity of the liquid is the same as that of the solid or the liquid is highly viscous or thixotropic, of course the material will not settle but even this does not prevent the process of the present invention from being carried out. However, the failure to settle would prevent separation by prior art means such as decantation. After a sufficient mixing time for the desired reaction or attachment to take place, an electromagnet, indicated generally by reference character 20 in FIG. 3, is inserted into the liquid. Electromagnet 20 is then energized by conventional means through wires 21 and the ferromagnetic particles are attracted to the tip 22 of the electromagnet 20 as shown in FIG. 4.

By de-energizing electromagnet 20, the particles will return to the bottom of the test tube as shown in FIG. 3. It is thus, of course, readily possible to convey the particles through a series of baths and if intimate contact is desired, the electromagnet can be de-energized and removed and the liquid and particles shaken for any desired period of time. By such techniques, a highly automated process can be devised utilizing an absolute minimum of human handling.

An alternate configuration of the ferromagnetic biomaterial support particle is shown in FIG. 5 where an iron sphere 25 is surrounded by a glass or ceramic layer 26. Another method of combining a glass or ceramic biomaterial support with a ferromagnetic substance is shown in FIG. 6 where an iron sphere 27 is attached to a ceramic sphere 28 by an adhesion 29.

The field of solid phase chemical reactions has received a great deal of attention in recent years. By the use of particles of the present invention, this field of chemistry can also provide an instantaneous controllable separation simply by the energizing and de-energizing of electromagnets. Although this process is shown as being carried on by immersing an electromagnet into the liquid, it, of course, can readily be carried out by placing the electromagnet along the exterior of the liquid container. Whereas filtration or centrifugation requires the user to move all of the liquid, by use of the present invention it is merely necessary to remove the solids and the liquid may remain essentially unmoved.

The mixing action of the process of the present invention is shown in FIGS. 7 and 8 of the drawings. A hollow cylindrical permanent magnet 30 surrounds the exterior of test tube 31 which holds a liquid 32 containing a plurality of particles 33 of the ferromagnetic biomaterial support of the present invention. By raising the magnet 30, the ferromagnetic particles 33 are moved upwardly in the liquid 32. If a sufficient amount of particles 33 is utilized, a complete bridge or barrier will be formed of the particles 33 in a manner shown in FIG. 7. By raising the magnet, the liquid is forced through the bed of particles and a unique mixing action is possible without the use of a separate agitation step.

Turning now to FIG. 9, this bed of ferromagnetic particles may utilized to form a bridge or valve to separate two liquids. As shown in FIG. 9, a liquid 35 is held away from liquid 36 by the bed of particles 37. The two liquids could be caused to mix either by lowering magnet 30 or by de-energizing the magnet. If magnet 30 were an electromagnet, this could be readily done by turning off the current. This valve action may be further improved by providing flat plate-like particles such as those shown in FIG. 10 and indicated by reference character 40.

It is not essential that the ferromagnetic particles be given a separate coat of a biomaterial support. For some chemicals the ferromagnetic particle itself could hold, attract or otherwise bond the desired reactant directly to its surface. An uncoated particle is indicated by reference character 41 in FIG. 11.

FIGS. 12 and 13 show a method for separating the ferromagnetic particles from the liquid 32 held in test tube 31. A second test tube 45 is placed over test tube 31 and magnet 30 is raised above the top of test tube 31. The ferromagnetic particles 33 are held within magnet 30 and are thus effectively removed from test tube 31. Test tube 45 may then be separated from test tube 31 and inverted as shown in FIG. 13 thereby effectively removing the solid particles 33 from the liquid 32 without the need for centrifugation, decantation or filtration.

The technique shown in FIGS. 12 and 13 may also be used to remove a precipitate from one container and convey it to a second container. This process may be brought about by placing ferromagnetic particles in the bottom of a test tube or other elongated container in a manner similar to that shown in FIG. 2 of the drawings. The second step would be to cause a precipitate to form in the liquid 15. This could be brought about in a conventional manner by adding a second reactant, by heating, chilling, seeding, bombarding with radioactive particles, ultraviolet light or by any process which would cause a solid to form in the liquid 15. The ferromagnetic particles could then be raised in a manner shown most clearly in FIGS. 7 and 8. In this way, the magnetic particles become a filter to draw out the precipitate from the liquid which in FIGS. 7 and 8 is referred to by reference character 32. By placing a test tube such as that shown in FIG. 12 and indicated by reference character 45 over the top of test tube 31 of FIG. 12 the precipitate could be effectively removed from liquid 32 and transferred to test tube 45. The precipitate could then be washed or otherwise treated and readily removed from the ferromagnetic particles by magnetic action or other more conventional means.

A unique feature of this method of filtration is its ability to be automated without the necessity of devising means for transferring the liquid 32 from its original container. Another unique feature of this method of filtration is its ability to hold the filter medium together without any resulting packing with its concomitant decrease in filter rate which is inherent with more conventional means of filtration such as vacuum filtration.

For filtration purposes, it is not necessary that a biomaterial support be affixed to the ferromagnetic material and uncoated ferromagnetic particles may be used. Alternatively, as suggested above, the ferromagnetic particles can be coated with a corrosion resistant or filter assisting medium and particles of different sizes may be utilized to control the degree of filtration desired.

Of course, additional mixing and separating steps may be carried out by utilizing test tubes larger than test tube 45 of FIG. 13 and inverting them over the top of tube 45 in a manner analogous to that shown in FIG. 12. In this way a complex series of steps may be carried out in a readily automated manner not heretofor possible.

Still further, the process of the present invention may be utilized to perform a filtration process where a solid is suspended in a liquid. The liquid suspension is placed in an elongated container and the ferromagnetic particles are added thereto and settle to the bottom of the liquid in a manner similar to that shown in FIG. 2 of the drawings. An exterior magnet could be positioned as shown in FIG. 13 of the drawings and raised upwardly along the exterior of the container in the manner indicated in FIGS. 7 and 8. Lastly, the solid could be completely removed from the container in a manner shown in FIG. 12 of the drawings. In this way, the precipitate is readily removed from the liquid which need never be transferred from its original container. Such a procedure is readily adapted to the performance of automated chemical analysis. A still further advantage of this method for automated materials handling is that the magnet and ferromagnetic particles are capable of lifting a container such as that indicated by reference character 45 in FIG. 12 without any additional holding means for container 45 since the magnetic attraction between the ferromagnetic particles and the magnet may be made sufficient to lift container 45. Further, by the use of electromagnets the container may be readily released by de-energizing the electromagnet.

Further adaptations of the filtration aspect of the present invention include the use of a filter aid with or above the ferromagnetic particles. For instance, a filter aid such as diatomaceous earth could be added to the container to which the ferromagnetic particles have first been added. For instance, a filter aid could be added to the tube shown in FIG. 2. The filter aid should, of course, be of sufficient gravity to settle and form an upper layer above particles 17 of FIG. 2. In this way gels or other difficult to separate particles could be more readily removed from the liquid 15.

The use of biologically active materials with solid phase chemistry shows great promise in performing processes not possible prior to this development. For instance, by attaching the enzyme asparaginase to a biomaterial support, the amino acid, asparagine, can be transformed into a chemical by-product. This technique shows promise for the treat of leukemia. The measurement of minute quantities of chemicals such as digoxin present in the blood of a user of digitalis is an example of a measurement made possible through the use of radioimmunoassay techniques. A known quantity of blood containing an unknown quantity of unradioactive digoxin are mixed with a bio-material support having an antibody adsorbed to its surface. The non-radioactive digoxin and the radioactive digoxin will compete for the digoxin antibody which is bound onto the ferromagnetic biomaterial support. The amount of binding of the radioactive digoxin can then be measured by the amount of radioactivity of the biomaterial spheres as compared to a known standard. The more the nonradioactive digoxin in the original sample, the less radioactive digoxin will have been coupled to the biomaterial support. In this way, a quantitative measurement of the amount of digoxin may be determined. The rendition of the biomaterial support ferromagnetic greatly facilitates the automation of such measurements. Similarly, immunoradiometric assay techniques may be used with the ferromagnetic biomaterial supports of the present invention.

The use of ferromagnetic biomaterial supports also permits solid phase reactions to be carried out in a fermentation bath where other separation techniques are very difficult. The separation of the support particles may be made more difficult either because the size of the fermentation bath prohibits centrifugation or decantation or because of the presence of other solid materials make filtration impractical. It is now possible to contact a fermentation broth with a desired enzyme and then remove the biomaterial support through electromagnetism. The enzyme can thus be removed from the fermentation bath and if necessary treated and reused rather than being discarded as is necessary with most processes.

Furthermore, particles of the same size can be separated by magnetic means which would be incapable of separation by filtration. The use of spheres of the type shown in FIG. 1 of the drawings has led to a highly reproduceable material which has been found difficult when large flat surfaces are coated with a biomaterial support substance.

While the term "biologically active" has been used in this specification, the present invention is not limited to biological materials and can also be used for other types of chemical reactions. For instance, a catalyst could be adsorbed to the ferromagnetic biomaterial support and added to a potentially reactive system. The support could then be removed by an electromagnet.

In vivo use of magnetic biomaterial support particles is possible since the positioning of the particles can be controlled from outside the body through the use of magnetism. Thus, the use of the present invention enables the user to position or hold particles to permit instant separation from reactants. The present invention is thus to be considered in all respects as illustrative and not restrictive, the scope of the invention being indicated by the appended claims rather than by the foregoing description. All changes which come within the meaning and range of equivalency of the claims therefore are intended to be embraced therein.

I claim:

1. A process of conveying a solid from one container to another comprising:
   placing a plurality of particles of a ferromagnetic substance in a test tube;
   moving a magnet near the outer surface of the first tube near the bottom end thereof;
   placing a collar over the open end of the tube; and
   moving the magnet upwardly along the tube to a point above the upper opening of the tube whereby the particles of a ferromagnetic substance and any substance entrapped thereby are moved into the collar.

2. The process of claim 1 wherein the diameter of said particles is between about one-tenth and 10 millimeters.

3. The process of claim 1 wherein the diameter of said particles is about one-half millimeter.

4. The process of claim 1 wherein said ferromagnetic material consists essentially of iron.

5. The process of claim 1 wherein said magnet is an electromagnet.

6. The process of claim 1 wherein said magnet is a permanent magnet.

7. The process of claim 1 wherein said particles have a biomaterial support affixed thereto.

8. The process of claim 1 wherein said collar is a portion of a second elongated container.

9. The process of claim 1 wherein said liquid contains a solid material and said particles are moved through said liquid thereby entrapping said solid material and removing it from said liquid.

10. The process of claim 1 wherein the test tube contains a liquid to which a filter aid has been added.

11. A process for conveying a solid from one container to another comprising:
    placing a plurality of particles of a ferromagnetic substance in a first test tube;
    moving a magnet near the outer surface of the first test tube near the bottom thereof;
    placing a second tube over the open end of the first tube; and
    moving the magnet upwardly along the first tube to a point above the upper opening of the first tube whereby the magnetic particles and any substance entrapped thereby are moved into the second tube.

* * * * *